United States Patent [19]

Randall

[11] 4,315,148

[45] Feb. 9, 1982

[54] METHOD AND APPARATUS FOR MEASURING NEUTRON CHARACTERISTICS OF MATERIAL SURROUNDING A BOREHOLE

[75] Inventor: Russel R. Randall, Houston, Tex.
[73] Assignee: Dresser Industries, Inc., Dallas, Tex.
[21] Appl. No.: 156,971
[22] Filed: Jun. 6, 1980
[51] Int. Cl.³ .............................................. G01V 5/00
[52] U.S. Cl. .................................. 250/262; 250/270
[58] Field of Search ....................... 250/262, 269, 270

[56] References Cited

U.S. PATENT DOCUMENTS

| | | | |
|---|---|---|---|
| 3,379,882 | 4/1968 | Youmans | 250/262 |
| 3,379,884 | 4/1968 | Youmans | 250/262 |
| 3,566,116 | 2/1971 | Nelligan | 250/262 |
| 4,046,764 | 9/1977 | Marquis | 250/262 |
| 4,223,218 | 9/1980 | Jacobson | 250/262 |
| 4,267,447 | 5/1981 | Johnstone | 250/262 |

Primary Examiner—Alfred E. Smith
Assistant Examiner—Janice A. Howell
Attorney, Agent, or Firm—Richard M. Byron; Patrick H. McCollum

[57] ABSTRACT

A pulsed source of fast neutrons and a radiation detector system are utilized in a well logging instrument, the detector being responsive to the thermal neutron population decay rate. The inverse of the decay rate is proportional to the measured macroscopic neutron absorption cross-section (Sigma). A Sigma is calculated by taking the natural logarithm of the ratio of the detected radiation counts occurring within two measurement intervals of fixed duration and starting at a fixed time after the neutron burst. This Sigma measurement provides a feedback voltage which is used in altering the starting time of two measurement intervals in a subsequent source pulsing cycle to provide a measured sigma value.

28 Claims, 8 Drawing Figures

METHOD AND APPARATUS FOR MEASURING NEUTRON CHARACTERISTICS OF MATERIAL SURROUNDING A BOREHOLE

BACKGROUND OF THE INVENTION

This invention relates, in general, to radioactivity well logging, and more particularly to methods and apparatus for determining the macroscopic thermal neutron absorption cross-section of the formations surrounding a borehole as determined by radiation measurements.

It is well known in the art of radioactivity well logging, for example, as illustrated and described in U.S. Pat. Nos. 3,379,882 and 3,379,884 which issued to Arthur H. Youmans and each of which is assigned to the assignee of the present invention, to measure the macroscopic thermal neutron capture cross-section [(Sigma (Σ)] of the formations surrounding a borehole. This prior art method makes such a measurement or computation by measuring the decline of the thermal neutron population in such formations within a fixed period of time following the emission of a burst of high energy neutrons and by dividing the radiations indicative of such thermal neutrons into two equal groups and computing the rate of change over the selected time interval. A second prior art method, as illustrated in U.S. Pat. No. 3,566,116, makes use of two measurement intervals. The starting time and the duration of the two measurement intervals are continuously adjusted so as to maintain a fixed counting ratio between the two measurement intervals.

SUMMARY OF THE INVENTION

In the preferred embodiment of the present invention, a calculation of the measurement of the decline of the thermal neutron population in the formation is derived by counting the detected radiation within two equal measurement intervals of fixed time duration and occurring at a fixed time after the neutron burst. A ratio of the two counting rates provide the rate of change over the selected time interval. The counting ratio is converted into a natural logarithm representative of the Sigma calculation.

The Sigma calculation derived by the ratio of the two fixed measurement intervals is utilized to vary the starting time of two fixed duration measurement intervals in a subsequent source pulsing cycle. In the preferred embodiment the first measurement interval will begin no earlier than 200 microseconds following the neutron burst and no later than 400 microseconds following the neutron burst. The second measurement interval will begin after and contiguous with the first measurement interval. The ratio is taken of the two counting rates within these intervals and is converted into the natural logarithm thereof. This measurement is recorded representing the macroscopic thermal neutron capture cross-section of the formation material.

Accordingly, it is a feature of the present invention to provide new and improved methods and apparatus for determining a macroscopic thermal neutron cross-section of formations surrounding earth boreholes;

It is also a feature of the present invention to provide new and improved methods and apparatus for varying the start time for measurement intervals used in determining a macroscopic thermal neutron cross-section;

It is yet another feature of the present invention to provide methods and apparatus for utilizing a macroscopic thermal neutron cross-section calculation for altering the starting time of measurement intervals within succeeding neutron source pulse cycles; and Still another feature of the present invention is to calculate the formation Sigma based on a ratio of the counting rates within two contiguous fixed measurement intervals and to use that Sigma calculation to set the starting time of two contiguous measurement intervals on a subsequent measurement cycle.

These and other features and advantages of the present invention can be understood from the following description of the techniques of producing the invention described in conjunction with the following drawings:

DETAILED DESCRIPTION OF THE DRAWINGS

Figure 1:
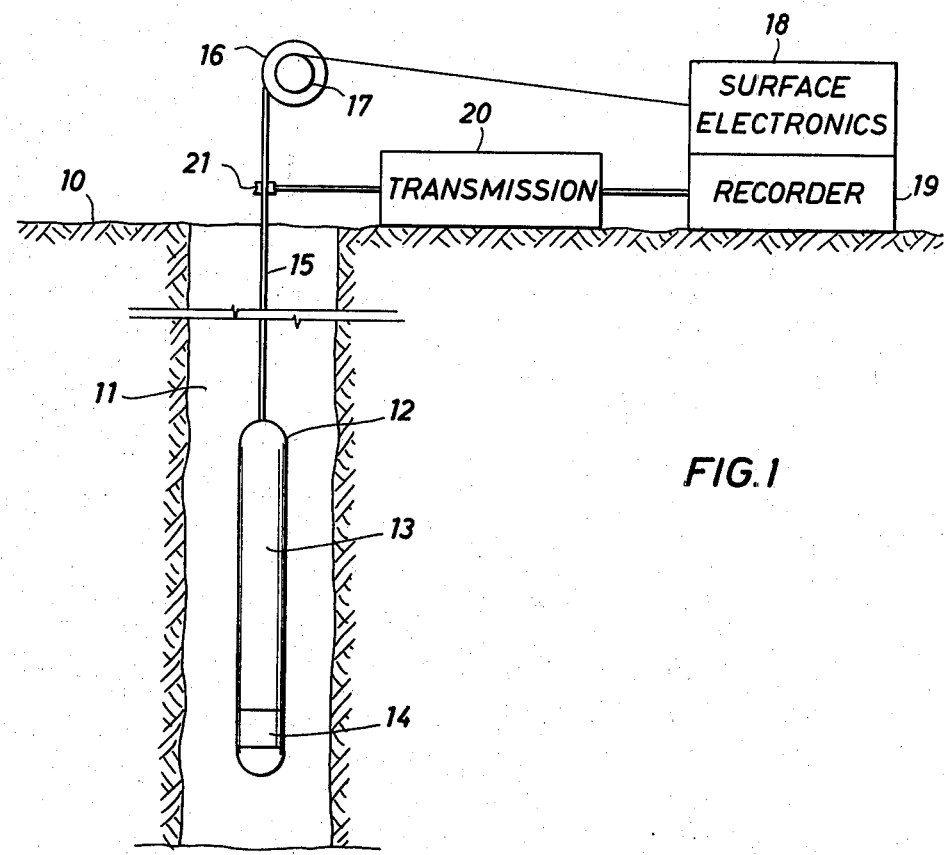
FIG. 1 is a side elevational view, partly in cross-section, of a radioactivity logging system in accordance with the present invention.

Referring now to the drawings in detail, particularly to FIG. 1, there is illustrated schematically a radioactivity well surveying operation in which a portion of the earth's surface 10 is shown in vertical section. An earth borehole 11 penetrates the earth's surface and may or may not be cased. Disposed within the well is subsurface instrument 12 of the well logging system. Subsurface instrument 12 comprises a detecting system 13 and a pulsed neutron source 14 for irradiating the formation with high energy neutrons. Cable 15 suspends the instrument 12 in the well and contains the required conductors for electrically connecting the instrument with the surface apparatus. The cable is wound on or unwound from drum 16 in raising and lowering the instrument 12 to traverse the well.

In making a radioactivity log of a well, instrument 12 is caused to traverse the well. Thereby neutrons from source 14 pulsedly irradiate the formations surrounding the borehole, and radiations influenced by the formations are detected by the detecting system 13. The resultant signal is sent to the surface through conductors within cable 15. Through slip rings and brushes 17 on the end of drum 16, the signals are coupled into surface electronics 18. After processing by the circuitry hereinafter described and illustrated, the resulting information is recorded on recorder 19. Recorder 19 is driven through transmission 20 by a measuring reel 21 over which cable 15 is drawn so that recorder 19 moves in correlation with the depth as instrument 12 traverses the well. The elements are shown diagrammatically, and it is understood that the associated circuits and power supplies are provided in a conventional manner. It is also understood that the housing for instrument 12 is constructed to withstand the pressures and mechanical and thermal abuses encountered in logging a deep well and to provide adequate space within it to house the necessary apparatus and to permit the transmission of radiation therethrough.

In the operation of the apparatus of FIG. 1, the source 14 is periodically activated, for example, every one thousand microseconds causing the formation to be irradiated with high energy neutrons. Gamma rays are detected by the detector system 13 which are indicative of thermal neutron reactions. The number of gamma rays present at any time is proportional to the thermal neutron population around the instrument 12. The decay rate of the neutron population is an exponential. Electrical signals are transmitted up cable 15 indicative of such detected gamma radiation.

In a homogeneous medium, the rate of thermal neutron is defined by the following equation:

$$N_2 = N_1 e^{-(\Delta t/T)} \qquad (1)$$

where $N_1$, $N_2$ are the number of thermal neutrons in existence at times $t_1$, and $t_2$; $t$ is the time between measurements $(t_2-t_1)$; and $T^{-1}$ is the absorption rate of thermal neutrons in the medium.

Thermal neutron capture cross-section of the medium is determined from the rate of absorption as follows:

$$\Sigma = (1/VT) \qquad (2)$$

where $\Sigma$ is the thermal neutron absorption cross-section and V is the velocity of thermal neutrons. Solving for sigma yields the familiar equation:

$$\Sigma = (1/V\Delta t) \cdot ln \cdot (N_1/N_2) \qquad (3)$$

Figure 2A:
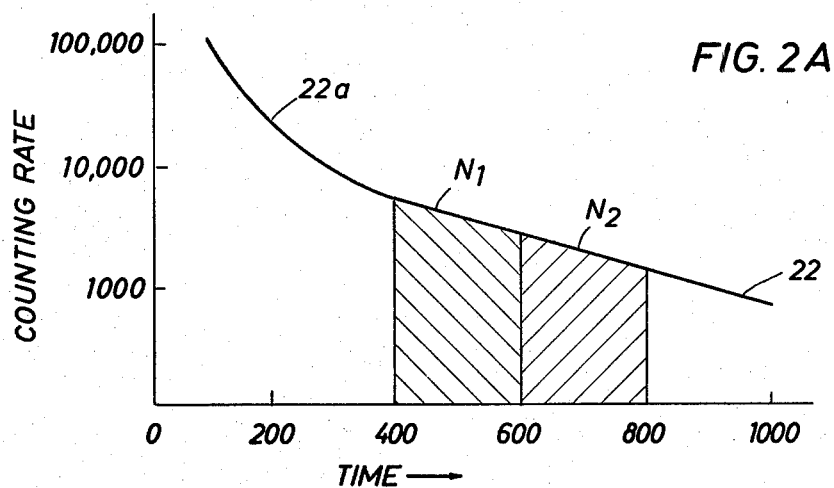
FIGS. 2A and 2B are schematic representations of the characteristic decay of a thermal neutron population following a burst of fast neutrons within a well and a method of utilizing the two gates to provide a measurement of the rate decline of the population.
Figure 2B:
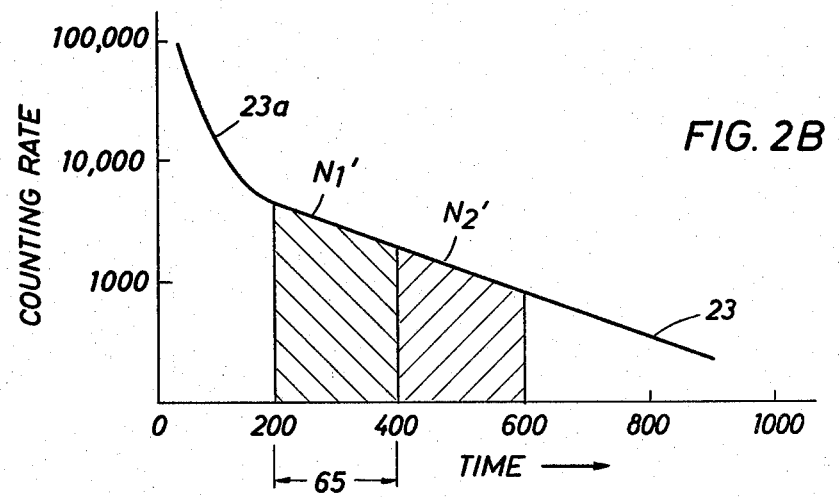

Referring now to FIGS. 2A and 2B, there is graphically illustrated a pair of waveforms 22 and 23 which are representative of the rate of neutron decay as measured by detector system 13 in accordance with the present invention. With the data which produces such curves, the rate of decline of the thermal neutron population is computed by measuring the integrated radiation counting rate under the curve 22 occurring during measure intervals $N_1$ and $N_2$ and beneath curve 23 during intervals $N_1'$ and $N_2'$. $\Delta t$ is measured between the midpoints or starts of the two measurement intervals and V is set to a constant value of 2200 meters/second. This is sufficient data to calculate Sigma.

As illustrated by decay rate curves 22, and 23, the initial rate of neutron decay is relatively complex. The initial rate of decrease of neutrons, as shown by portions 22a and 23a of curves 22, is a function of the relation between borehole materials and the Sigma value of the formation. These borehole materials include the tool housing, the fluid in the casing, the casing, and the cement or fluid around the casing. After some time period these transient influences diminish and the neutron decay curves 22 and 23 become exponential and are substantially controlled by the formation capture cross-section. Since the rate of neutron decay is exponential, a straight line on a semi-logarithmic scale, only two time referenced measurements are necessary to determine Sigma.

Figure 3:
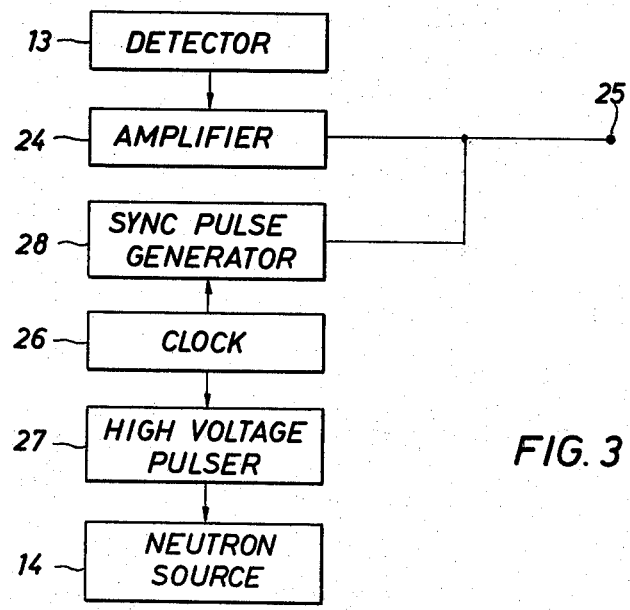
FIG. 3 illustrates in block diagram a portion of the surface electronics in accordance with the present invention.

Referring now to FIG. 3, there is illustrated the subsurface circuitry for generating the sync signals and signal pulses hereinafter illustrated and described. The dectector 13 is coupled to an amplifier 24, whose output is connected to junction 25. A clock circuit 26 has its output connected to a high voltage pulser 27 which drives a conventional neutron source 14. In the preferred embodiment of the present invention, source 14 is a conventional D-T accelerator producing high energy 14 Mev neutrons at a rate as determined by the clock 26. The discrete burst of neutrons occur 1000 microseconds apart and are generally of 10 to 50 microseconds duration. Clock circuit 26 also drives a sync generator 28 having its output connected to junction 25. The junction 25 is connected to a conductor of cable 15 and serves to carry the signals to surface electronics 18 for processing.

In the operation of the circuitry and apparatus illustrated in FIG. 3, the clock 26 causes high voltage to be applied to neutron source 14 to generate discrete bursts of neutrons, each such burst being separated by approximately 1000 microseconds. The detector 13 detects gamma radiation resulting from the capture of thermal neutrons occasioned in the formation surrounding the borehole by neutron source 14. The detected pulses from detector 13 are immediately amplified by amplifier 24 and combined with the sync pulses, generated by sync pulse generator 28 in response to clock 26, for transmission to the earth's surface.

Figure 4:
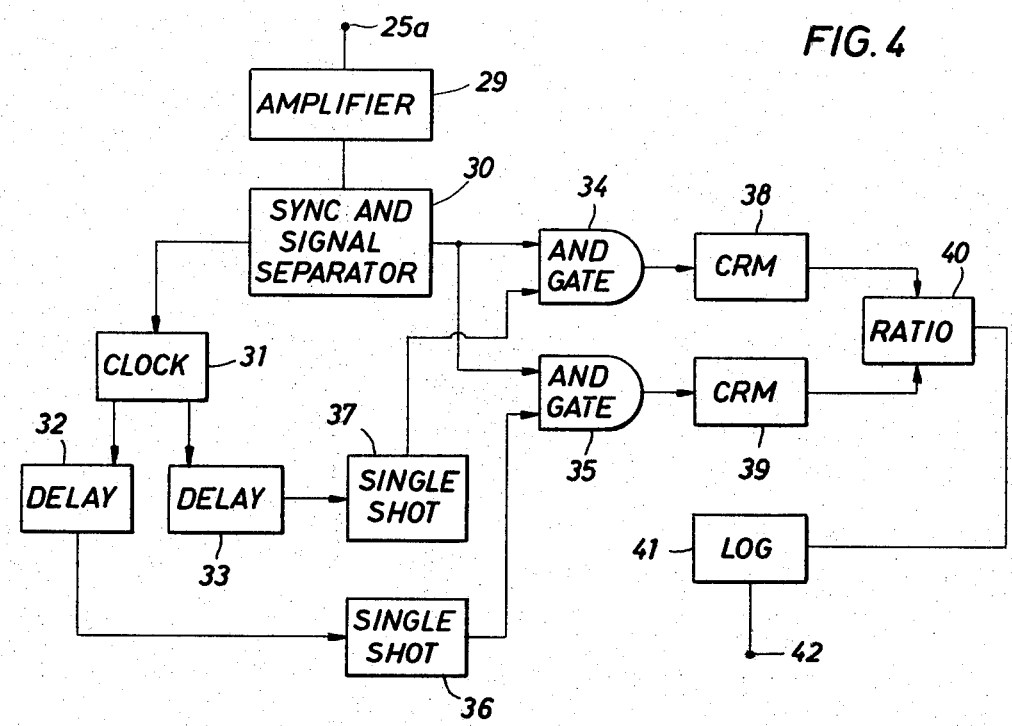
FIG. 4 illustrates in block diagram additional surface electronics in accordance with the present invention.

Referring now to FIG. 4, a portion of the surface electronics shown generally by the reference numeral 18 in FIG. 1 is shown in greater detail. The junction 25a corresponds to the junction 25 in the subsurface circuitry. Junction 25a is coupled through an amplifier 29 to a conventional sync and signal separator circuit 30 which separates the sync signal from the amplified signal pulses. The separation can be achieved by any of the conventional circuit devices, for example, through pulse height discrimination. The sync output of the separator circuit 30 is coupled into clock circuit 31 the output of which is connected to the input of delay circuits 32 and 33. The signal output of separator circuit 30 is coupled into one input of a two-input AND gate 34 and into one input of a second two-input AND gate 35.

Delay circuit 32 is set to have a delay of 400 microseconds and has the output connected to single shot multivibrator 36. Delay circuit 33 is set to have a delay of 600 microseconds and has the output connected to single shot multivibrator 37. Each of the single shot multivibrators 36 and 37 produces a square wave of 200 microseconds duration. The output of single shot multivibrator 36 is connected to the second input of AND gate 35 while the output of single shot multivibrator 37 is connected to the second input of AND gate 34. The output of AND gate 34 is connected to count rate meter 38 and the output of AND gate 35 is connected to count rate meter 39. The outputs of count rate meters 38 and 39 provide the inputs to ratio circuit 40 the output of which is connected to logarithmic circuit 41. The output of logarithmic circuit 41 is connected to junction 42.

In the operation of the surface electronics illustrated in FIG. 4, the sync signal and the detected radiation pulses are provided by subsurface instrument 12 to amplifier 29. The amplified output of amplifier 29 is coupled to sync and signal circuitry 30 the sync output of which is coupled to clock circuit 31 and the signal output representative of the detected radiations is connected to one input of AND gates 34 and 35. The clock output signal from clock circuit is delayed 400 microseconds by delay circuit 32 and is delayed 600 microseconds by delay circuit 33. The delayed clock signal output from delay circuit 32 is coupled to single shot multivibrator 36 while the delayed clock signal output from delay circuit 33 is coupled to single shot multivibrator 37.

Single shot multivibrators 36 and 37 are set to produce a square wave output of 200 microseconds in duration. The output of single shot multivibrator 36 provides the second input to AND gate 35 whereas the output of single shot multivibrator provides the second input to AND gate 34. Thus, AND gate 35 will pass all the detected radiation occurring in the time interval from 400–600 microseconds following the sync pulse and AND gate 37 will pass all the detected radiation occurring in the 600–800 microsecond interval. The respective radiation intervals are illustrated by measurement intervals $N_1$ and $N_2$ of FIG. 2A.

The outputs of AND gate 34 and AND gate 35 are counted by count rate meters 38 and 39, respectively. A ratio is taken by ratio circuit 40 of the counts within the two measurement intervals. The logarithmic circuit 41 provides a natural logarithmic signal of the ratio signal from ratio circuit 40. The output of logarithmic circuit 41 is connected to junction 42 and is the Sigma value of the formation.

Figure 5:
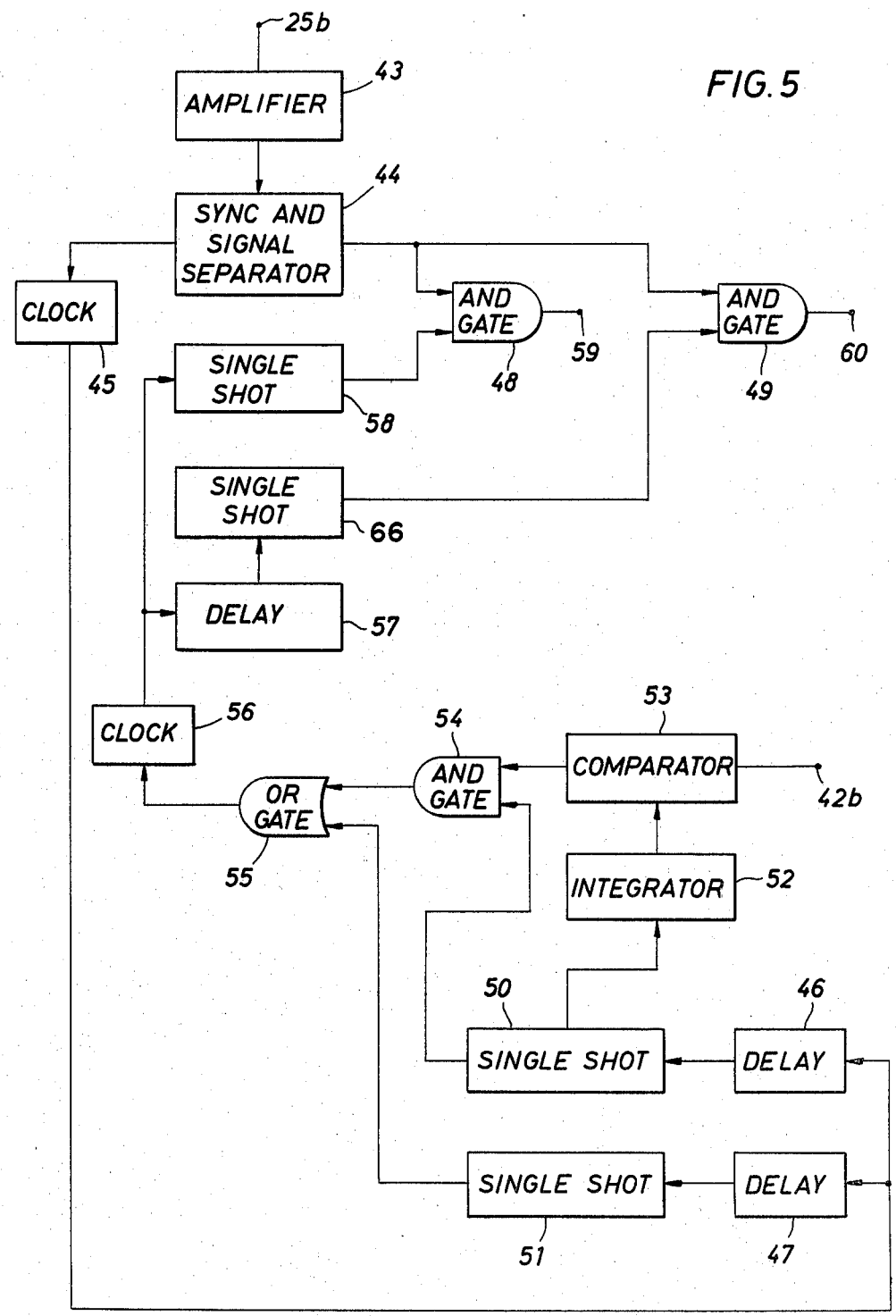
FIG. 5 illustrates in block diagram additional surface electronics utilized in accordance with the present invention.

Referring now to FIG. 5 a second portion of the surface electronics shown generally by the reference numeral 18 in FIG. 1 is shown in greater detail. The junction 25b corresponds to the junction 25 in the subsurface circuitry. The junction 25b is coupled through an amplifier 43 to a conventional sync and signal separator circuit 44 which separates the sync signal from the amplified signal pulses. The separation can be achieved by any of the conventional circuit devices, for example, through pulseheight discrimination. The sync output of the separator circuit 44 is coupled into clock circuit 45 the output of which is connected to the input of delay circuits 46 and 47, the operation of which will be hereinafter explained in detail. The signal output of separator circuit 44 is coupled into one input of a two input AND gate 48 and into one input of a second two-input AND gate 49.

Delay circuit 46 is set to have a delay of 200 microseconds and has the output coupled to single shot multivibrator 50. Delay circuit 47 is set to have a delay of 400 microseconds and has the output coupled to single shot multivibrator 51. Each of the single shot multivibrators 50 and 51 produces a square wave of 200 microseconds duration. One output of single shot multivibrator 50 is connected to integrator circuit 52 where the 200 microsecond gate provided by single shot multivibrator 50 is converted into a d.c. level proportional over time to the width of the input gate. The output from integrator 52 is connected to comparator 53 which has a second d.c. level input 42b which coincides with junction 42 of FIG. 4.

The output of comparator 53 is connected to one input of a two-input AND gate 54. The other input to AND gate 54 is provided by the output of single shot multivibrator 50. The output of AND gate 54 is connected to one input of a two-input OR gate 55 of which the second input is the output from single shot multivibrator 51. The output of OR gate 55 provides the input to clock circuit 56.

Clock circuit 56 is connected to the input of delay circuit 57 and is also connected to the input single shot multivibrator 58. The output of delay circuit 57 is connected to the input of single shot multivibrator 66 the output of which is connected to one input of two-input AND gate 49. The output of single shot multivibrator 58 is connected to one input of two-input AND gate 48. The output of AND gate 48 is connected to junction 59 and the output of AND gate 49 is connected to junction 60.

In the operation of the portion of the surface electronics illustrated in FIG. 5, the sync signal and the detected pulses are supplied by the subsurface instrument 12 to amplifier 43. The amplified output of amplifier 43 is coupled to sync and signal circuitry 44 the sync output of which is coupled to clock circuit 45 and the signal output representative of the detected radiations is connected to one input of the two-input AND gates 48 and 49. The clock output signal from clock circuit 45 is delayed 200 microseconds by delay circuit 46 and 400 microseconds by delay circuit 47. The delayed clock signal output from delay circuit 46 is coupled to single shot multivibrator 50 while the delayed clock signal output from delay circuit 47 is coupled to single shot multivibrator 51.

Single shot multivibrator 50 produces a square wave of 200 microseconds in duration which provides the input to integrator circuit 52. The square wave input to integrator is converted to a d.c. level in the form of a d.c. voltage ramp which is proportional over time to the width of the input gate. The slope of the integrator output ramp can be set to provide the desired time constant for optimum use in comparator 53. In addition to the d.c. voltage ramp input comparator 53 is supplied with a second input from junction 42b which is a d.c. voltage level proportional to the calculated Sigma of the measured formation. The source of the Sigma measurement at junction 42b is the portion of the surface electronics illustrated in FIG. 4 and is the Sigma calculated within the fixed measurement intervals of 400–600 microseconds and 600–800 microseconds.

Comparator circuit 53 will produce an output at the point where the Sigma level and the integrator voltage level are in coincidence. The comparator output is connected to one input of AND gate 54, the second input being the 200 microsecond gate output from single shot multivibrator 50. AND gate 54 will produce an output whenever there is coincidence within comparator 53 and this coincidence occurs within the interval from 200–400 microseconds following the sync pulse. The output of AND gate 54 is connected to one input of OR gate 55 the second input being a 200 microsecond gate signal starting 400 microseconds after the sync signal. If OR gate 55 is not triggered by the output of AND gate 54 by the expiration of 400 microseconds after the sync pulse, single shot multivibrator 51 will cause OR gate 55 to output a signal at the 400 microsecond point in time.

The output signal from OR gate 55 is connected to clock circuit 56 the output of which is connected to single shot multivibrator 58 and delay circuit 57. Single shot multivibrator will provide an output square wave signal 200 microseconds in duration, the square wave starting at a time between 200–400 microseconds following the sync pulse. The square wave output provides the second input to AND gate 48 the output of which will be all detected radiation occurring within the time interval of the square wave input. Delay circuit 57 provides a delay of 200 microseconds after which single shot multivibrator 66 is caused to output a square wave signal of 200 microseconds in duration. The square wave output of single shot multivibrator 66 supplies the second input to AND gate 49 so that AND gate 49 will output all the detected radiation within the gate inverval of single shot multivibrator 59.

Figure 6:
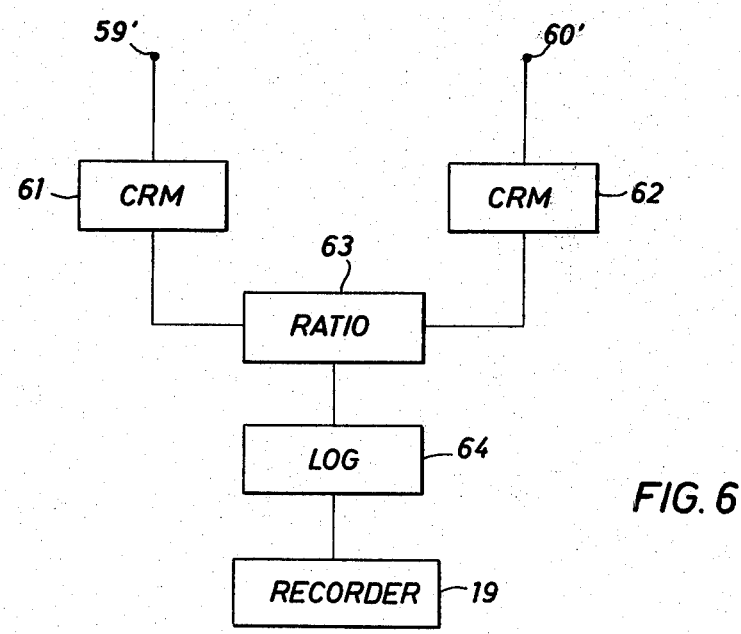
FIG. 6 illustrates in block diagram additional surface electronics in accordance with the present invention.

In FIG. 5, output junctions 59 and 60 correspond to junctions 59' and 60' of FIG. 6. The detected radiations within the interval provided by AND gate 48 are coupled to count rate meter 61 and the detected radiations within the second interval provided by AND gate 49 coupled to count rate meter 62. The count rate meters 61 and 62 are connected to ratio circuit 63. The ratio circuit 63 is connected to logarithmic circuit 64. The output of the logarithmic circuit 64 is connected to recorder 19.

Figure 2C:
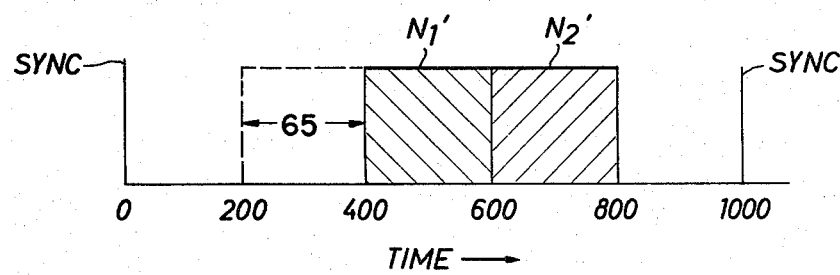
FIG. 2C schematically illustrates the variable starting time relative to the sync pulse of the measurement intervals.

In the operation of the circuitry of FIG. 6, the detected radiation pulses counted by count rate meter 61 represent all the detected radiation occurring with a first time interval, represented by $N_1'$ of FIG. 2B. This interval is 200 microseconds in duration and will begin at some time between 200 and 400 microseconds after the sync pulse. The detected radiation pulses counted by count rate meter 62 represent all the detected radiation occurring within a second time interval, $N_2'$ of FIG. 2, which is of equal duration to the first interval and begins contiguous with the termination of the first interval.

Ratio circuit 63 provides a ratio of the first and second gate signals. The logarithmic circuit 64 provides a natural logarithmic signal of the ratio signal from ratio circuit 63. The output of logarithmic circuit 64 is the Sigma value of the formation. The Sigma value calculated from the movable gate intervals is recorded by means of recorder 19.

Returning now to FIG. 2 and recalling the previous discussion, the rate of neutron decay curve, 22 and 23, has an initial rate of neutron decay, 22a and 23a, which is not an exponential function but rather is relatively a complex function caused in part by borehole influences. After some short period of time these disturbing influences become negligible and the rate of decay is substantially controlled by the formation capture cross-section. The point at which the undesirable influences become negligible is related to the rate of decline in the neutron population. To increase measurement accuracy, partly based on a higher counting rate of detected radiation, it is desirable to begin counting the detected radiation early on the exponential portion of the delay curve. Therefore, as the calculated Sigma value for the formation, as supplied from the fixed measurement intervals, increases it is desirable to reduce the point in time on the rate of decay curve at which the measurement of detected radiation begins.

As discussed in relation to the circuit drawings, the starting time in relation to the sync pulse is altered by a function of the previously calculated Sigma value. The first measure interval $N_1'$ is allowed to begin by the output provided by AND gate 54 which can range as early in time as 200 microseconds following the sync pulse. If AND gate 48 does not provide an output OR gate 55 will assure the measure interval to begin no later than 400 microseconds following the sync pulse. In other words, measure interval $N_1'$ will begin within time interval 65 illustrated in FIG. 2C. Measure interval $N_2'$ is caused to begin immediately upon the trailing edge of interval $N_1'$ so that the two measure intervals are contiguous.

Thus, there has been described and illustrated herein a new and improved method and apparatus for measuring thermal neutron decay times. Those skilled in the art will recognize that numerous other variations and modifications may be made without departing from the scope of the present invention. For example, delay circuit 51 could provide measurement intervals will not be contiguous but rather would be separated by some fixed time. Likewise, the present invention could be applied when using a dual detector neutron logging instrument.

The embodiment of the invention in which an exclusive property or privilege is claimed are defined as follows:

1. A method for logging the formations surrounding an earth borehole, comprising:
   pulsedly irradiating said formations with discrete bursts from a source of high energy neutrons;
   detecting radiations emanating from said irradiated formations at a detector spaced from said source;
   measuring said detected radiations during first and second fixed time duration intervals following a burst from said source;
   measuring said detected radiations during third and fourth fixed time duration intervals following a subsequent burst from said source; and
   controlling automatically the starting time of said third and fourth measurement intervals in accordance with said measurement from said first and said second time intervals.

2. The method for logging of claim 1 wherein said third and said fourth time intervals are contiguous and of equal duration.

3. The method for logging of claim 2 wherein said third time interval is automatically controlled to start from between 200–400 microseconds following said subsequent neutron burst and said fourth time interval is controlled to start from between 400–600 microseconds following said subsequent neutron burst.

4. The method for logging of claim 3 wherein said first and said second time intervals are contiguous and of equal duration.

5. The method for logging of claim 4 wherein said first time interval is from between 400–600 microseconds after said burst of high energy neutrons and said second time interval is from between 600–800 microseconds following said burst of high energy neutrons.

6. The method for logging of claim 5 wherein said bursts of high energy neutrons are 1000 microseconds apart.

7. The method for logging of claim 6 further comprising deriving a ratio of said measured radiations during said first and said second intervals, said ratio being substantially representative of the decline of the neutron population in said formations.

8. The method for logging of claim 7 further comprising deriving a ratio of said measured radiations during said third and said fourth intervals, said ratio being substantially representative of the decline of the neutron population in said formations.

9. The method for logging of claim 8 wherein said ratio of said third and said fourth intervals is recorded in relation to borehole depth.

10. A method for determining the macroscopic neutron absorption cross-section of earth formations surrounding a borehole, comprising:
    irradiating said formations with at least two bursts of high energy neutrons;

detecting secondary radiations from said formations at a point spaced from the source of said irradiation;

generating a first electrical signal indicative of the secondary radiation detected occurring during first and second fixed time duration intervals following a first burst of high energy neutrons;

generating a second electrical signal indicative of the secondary radiations detected occurring during third and fourth fixed time duration intervals following a second burst of high energy neutrons, the starting time of said third interval being automatically controlled by said first electrical signal.

11. The method of claim 10 wherein said third time interval is controlled to begin from between 200–400 microseconds following said neutron burst.

12. The method of claim 11 wherein said third and said fourth time intervals are contiguous and of equal duration.

13. The method of claim 12 wherein said third and said fourth time intervals are of 200 microseconds in duration.

14. The method of claim 13 wherein said first and said second time intervals are contiguous and of equal duration.

15. The method of claim 14 wherein said bursts of high energy neutrons are approximately 1000 microseconds apart and said first time interval is from between 400–600 microseconds after said burst and said second time interval is from between 600–800 microseconds following said burst.

16. The method of claim 15 wherein said first electrical signal represents the ratio of said radiation within said first and said second intervals and said second signal represents the ratio of said radiation within said third and said fourth intervals.

17. Apparatus for logging the formations surrounding an earth borehole, comprising:
an elongated instrument adopted to traverse on earth borehole;
a pulsed source of high energy neutrons in said instrument for emitting bursts of high energy neutrons;
a radiation detector in said instrument for detecting radiation emanating from said irradiated formations;
means for measuring said detected radiations during first and second fixed time duration intervals following a burst of neutrons from said source;
means for measuring said detected radiations during third and fourth fixed time duration intervals following a subsequent burst from said source; and
means for automatically controlling the starting time of said third measurement interval in accordance with said measurement from said first and second intervals.

18. The apparatus according to claim 17 further comprising means for starting said fourth time interval contiguous with said third time interval.

19. The apparatus of claim 18 wherein said third and said fourth time intervals are of equal time duration.

20. The apparatus of claim 19 wherein said third time interval is controlled to start from between 200–400 microseconds following said neutron burst.

21. The apparatus of claim 20 wherein said third and said fourth time intervals are 200 microseconds in duration.

22. The apparatus of claim 21 wherein said first and said second time intervals are contiguous and of equal duration.

23. The apparatus of claim 22 wherein said first and second time intervals are 200 microseconds in duration.

24. The apparatus of claim 23 wherein said bursts of high energy neutrons are 1000 microseconds apart.

25. Apparatus for logging the formations surrounding an earth borehole, comprising:
a source for pulsedly irradiating said formations with discrete bursts from a source of high energy neutrons;
a detector for detecting radiations emanating from said irradiated formations;
means for generating electrical signals indicative of said detected radiations;
means for gating said electrical signals indicative of said detected radiation for a first time interval following each of said bursts of high energy neutrons;
means for gating said electrical signals indicative of said detected radiation for a second time interval following each of said bursts of high energy neutrons;
means for gating said electrical signals indicative of said detected radiation for a third time interval following each of said bursts of high energy neutrons;
means for gating said electrical signals indicative of said detected radiation for a fourth time interval following each of said bursts of high energy neutrons;
means for automatically controlling the starting time of said third and said fourth time intervals in response to said electrical signals from said first and said second time intervals derived from a preceeding irradiation interval.

26. The apparatus of claim 25 further comprising means for deriving a ratio of said electrical signals from said first time interval and said electrical signals from said second time interval, said ratio being substantially representative of the decline of the neutron population in said formation.

27. The apparatus of claim 26 further comprising means for deriving a ratio of said electrical signals from said third time interval and said electrical signals from said fourth time interval, said ratio being substantially representative of the decline of the neutron population in said formation.

28. The apparatus of claim 27 further comprising means for recording said ratio derived from said third and said fourth electrical signals.

* * * * *